United States Patent [19]

Righter

[11] Patent Number: 5,226,425
[45] Date of Patent: Jul. 13, 1993

[54] PORTABLE ECG MONITOR/RECORDER

[75] Inventor: William H. Righter, Aloha, Oreg.

[73] Assignee: Ralin, Inc., Bannockburn, Ill.

[21] Appl. No.: 983,798

[22] Filed: Nov. 30, 1992

Related U.S. Application Data

[62] Division of Ser. No. 757,254, Sep. 10, 1991, Pat. No. 5,191,891.

[51] Int. Cl.⁵ ............................................. A61B 5/04
[52] U.S. Cl. .................................... 128/710; 128/904; 128/709; 128/706; 128/702
[58] Field of Search ............... 128/696, 702, 706, 709, 128/904, 690

[56] References Cited

U.S. PATENT DOCUMENTS

| | | | |
|---|---|---|---|
| 3,819,863 | 6/1974 | Slaght | 128/904 |
| 3,872,252 | 3/1975 | Malchman et al. | 128/697 |
| 3,938,507 | 2/1976 | Sarnoff et al. | 128/701 |
| 4,055,729 | 10/1977 | Vandling | 358/434 |
| 4,120,294 | 10/1978 | Wolfe | 128/706 |
| 4,221,223 | 9/1980 | Linden | 128/706 |
| 4,337,377 | 6/1982 | Van Riper et al. | 128/904 |
| 4,489,731 | 12/1984 | Baumberg | 128/690 |
| 4,531,527 | 7/1985 | Reinhold, Jr. et al. | 128/696 |
| 4,535,783 | 8/1985 | Marangoni | 128/711 |
| 4,606,352 | 8/1986 | Geddes et al. | 128/702 |
| 4,622,979 | 11/1986 | Katchis et al. | 128/904 |
| 4,802,008 | 1/1989 | Walling | 358/141 |
| 4,858,617 | 8/1989 | Sanders | 128/696 |
| 4,862,896 | 9/1989 | Reinhold, Jr. et al. | 128/696 |
| 4,889,134 | 12/1989 | Greenwold et al. | 128/696 |
| 4,938,228 | 7/1990 | Righter et al. | 128/690 |
| 4,974,607 | 12/1990 | Miwa | 128/904 |
| 4,991,200 | 2/1991 | Lin | 379/100 |
| 5,029,590 | 7/1991 | Allain et al. | 128/710 |
| 5,041,918 | 8/1991 | Ishida et al. | 358/442 |
| 5,050,612 | 9/1991 | Matsumura | 128/696 |

OTHER PUBLICATIONS

Tompkins, Willia J., "Patient Worn, Intelligent Arrythmia Systems," *IEEE Engineering In Medicine and Biology Magazine*, Dec. 1985, pp. 38-42.

Primary Examiner—Kyle L. Howell
Assistant Examiner—George Manuel
Attorney, Agent, or Firm—Leydig, Voit & Mayer

[57] ABSTRACT

A portable apparatus having electronic circuitry for selectively monitoring and recording a user's ECG signals, wherein a first conductive electrode is disposed on a first surface of the apparatus casing for contact with an ECG lead position on the user's body and second and third electrodes are disposed on at least one other surface of the casing for ease of contact by a thumb and finger, respectively, of the user's hand. One of the second and third electrodes provides a ground signal source for the electronic circuitry. A wristband is provided for securing the apparatus to the user's wrist and a microprocessor controls the electronic circuitry such that the user's ECG signal is monitored/recorded only when the user grasps the second and third electrodes. A separate modem device is attachable to the apparatus for effecting burst mode transmission of data to an external receiver.

33 Claims, 5 Drawing Sheets

PORTABLE ECG MONITOR/RECORDER

This is a divisional of copending application Ser. No. 07/757,254, filed on Sep. 10, 1991 now U.S. Pat. No. 5,191,891.

FIELD OF THE INVENTION

The present invention relates to an apparatus for monitoring and recording ECG data, and more particularly to a self-contained, portable ECG monitor/recorder.

BACKGROUND OF THE INVENTION

Portable electrocardiogram (ECG) monitoring and recording devices for use by persons in out-patient (e.g., home or work) environments have long been known Recently, compact devices have been developed that may be worn or carried by a user for monitoring and recording ECG data and transmitting the recorded data through a telephone handset to analyzing equipment at a doctor's office or centralized location. These devices each provide certain benefits, but also suffer from various short-comings and deficiencies. These deficiencies relate primarily to either the physical size of the units or to the way in which the user is required to make contact with the electrodes and subsequently activate the recording sequence.

For example, with some of these known devices the user is required to apply the device (particularly its electrodes) to a body portion (e.g., bare chest) as soon as possible after the on-set of episodic symptoms, such as an arrhythmia. Of course, given the practical delays in finding the unit, locating a private place in which to effect the recording, opening or removing a chest-covering shirt or blouse, applying the unit to the chest and pushing the record button, transient episodic symptoms are often missed.

Other devices have attempted to overcome these "missed-event" deficiencies by requiring the user to apply two or more paste-on electrodes to their body, which electrodes are wired into the device. The unit is worn attached to the user's clothing and a memory loop feature is employed which allows the user ample time to activate the recording sequence after the on-set of episodic symptoms. Since the user actually wears attached electrodes, continuous monitoring is possible and the memory loop ensures that transient ECG data is rarely missed. Patients, however, are generally resistent to wearing either paste-on electrodes or a bulky device attached to their clothing. The paste-on electrodes become uncomfortable over extended periods of time, and the size and placement of the unit on the outside of clothing draws unwanted attention to the patient's medical condition.

U.S. Pat. No. 4,120,294 (Wolfe) discloses a wrist-worn device for monitoring electrical heart signals (e.g., heartbeat rate or ECG), but does not include memory for recording such data. Moreover, the Wolfe unit has only two electrodes—no ground electrode is contemplated—and, therefore, is highly susceptible to muscle artifact signals which can degrade the quality of ECG data pickup. Consequently, even if memory was provided, recording of medical-grade ECG data by such a unit would be unlikely.

SUMMARY OF THE INVENTION

In view of the foregoing, it is a primary object of the present invention to provide an apparatus that records medical-grade ECG data and yet is convenient and comfortable for a user to wear.

A related object of the present invention is to provide a portable ECG recorder which does not utilize paste-on electrodes.

Another object of the present invention is to provide a portable ECG recorder which operates so as to ensure long battery life.

A further object of the present invention is to provide a portable ECG recorder and a separate, attachable modem device for transmitting stored data from the recorder to a receiving station.

A related object of the present invention is to provide an ECG recorder which transfers data to a separate modem in burst mode.

Yet another object of the present invention is to provide a portable ECG recorder having a high common mode rejection ratio through use of a three electrode configuration and improved circuit means.

Other objects and advantages of the present invention will become apparent from the following detailed description when taken in conjunction with the drawings, in which:

While the invention will be described in connection with certain preferred embodiments, there is no intent to limit it to those embodiments. On the contrary, the intent is to cover all alternatives, modifications and equivalents included within the spirit and scope of the invention as defined by the appended claims.

DETAILED DESCRIPTION OF THE PREFERRED EMBODIMENTS

Figure 1A:
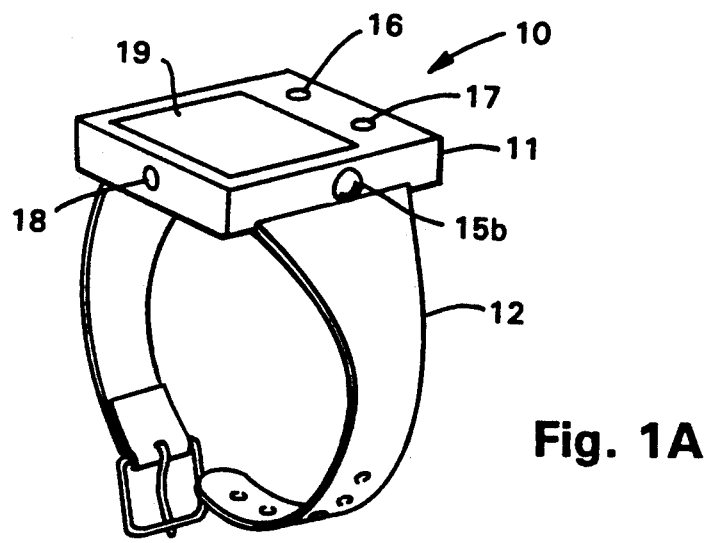
FIG. 1A is a perspective view of a portable EGG monitor/recorder exemplified by the present invention.

Turning now to the drawings, and referring first to FIG. 1A, there is shown a portable ECG monitor/recorder 10 which is adapted to be worn on the wrist of a user. This unit includes a casing 11 which houses the electronic circuitry and a wristband 12 for securing the casing to the user's wrist. The casing 11 includes surface-mounted electrodes which the user contacts to obtain a conventional Lead I ECG measurement (i.e., differentially across the user's arms), control buttons, an output port for coupling the unit to a modem device, and an LCD display for visually providing information to the user.

Figure 1B:
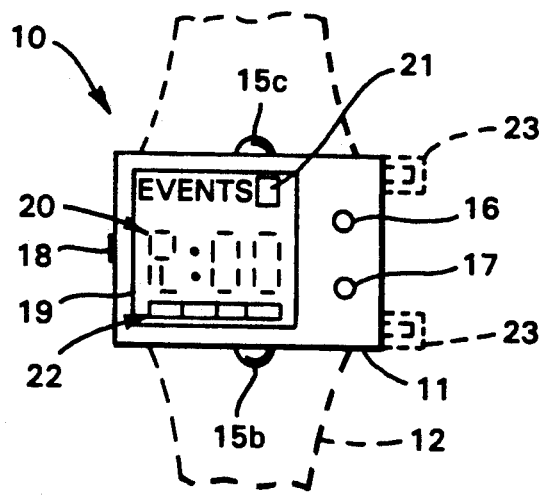
FIG. 1B is a top view of the ECG monitor/recorder of FIG. 1A.
Figure 1C:
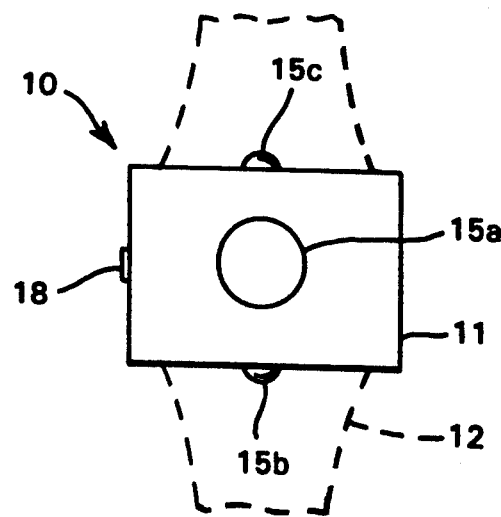
FIG. 1C is a bottom view of the ECG monitor/recorder of FIG. 1A.

As shown in FIGS. 1A–1C, a first conductive electrode 15a is provided on the bottom surface of the casing 11, where it is held in constant contact with the user's wrist when the unit is worn. Another pair of conductive electrodes 15b, 15c are provided on opposing side surfaces of the casing 11, where they can be easily contacted by the thumb and forefinger, respectively, of the user's right hand (assuming the unit is being worn on the left wrist). By grasping this pair of electrodes 15b, 15c, the user completes the Lead I circuit and activates the internal electronic circuitry, as will be described in further detail hereinafter, such that recording of the ECG data commences.

All three electrodes are made of a suitable conducting material, preferably silver or silver chloride, and to reduce undesirable electrode-skin artifact "noise" signals arising from contact variations, at least the side electrodes 15b, 15c are substantially circular or oval, as opposed to square or rectangular, are small enough in size to be covered completely by the user's finger and/or thumb, and have a curved, as opposed to flat, surface geometry. To enhance the electrical contact between the first electrode 15a and the user's wrist, the user typically prepares the skin contact area by applying an appropriate contact cream or gel (or even water or saliva) before securing the unit to the wrist.

The unit further includes a pair of push-buttons 16, 17 on its top surface, one of which is used to clear the unit's memory and the other being used to transmit data stored in the memory to a separate modem device via serial output port 18.

An LCD display 19 is also provided on the top surface of the casing. This display visually provides information to the user, preferably including an indicator 20 of the time of day, an indicator 21 of the number of cardiac events (e.g., arrhythmias) recorded, and a bar graph 22 which indicates the portion of the total memory that is filled with data.

While the inventive ECG monitor/recorder will preferably be used in an embodiment having a wristband for securing the casing to the user's wrist (as shown in FIG. 1A), it will be readily appreciated that the unit is easily adapted so that it can be worn by the user as a pendant. Specifically, rather than having a wristband 12, the casing 11 is provided with a pair of integral eyelets 23 (shown in phantom in FIG. 1B) for attachment to a cord or chain so that the unit can be hung around the user's neck. As such, the first electrode 15a is disposed to facilitate electrical contact with an ECG lead position on the user's chest, and the other two electrodes 15b, 15c can still be easily grasped by the user at the on-set of a cardiac event.

Figure 2:
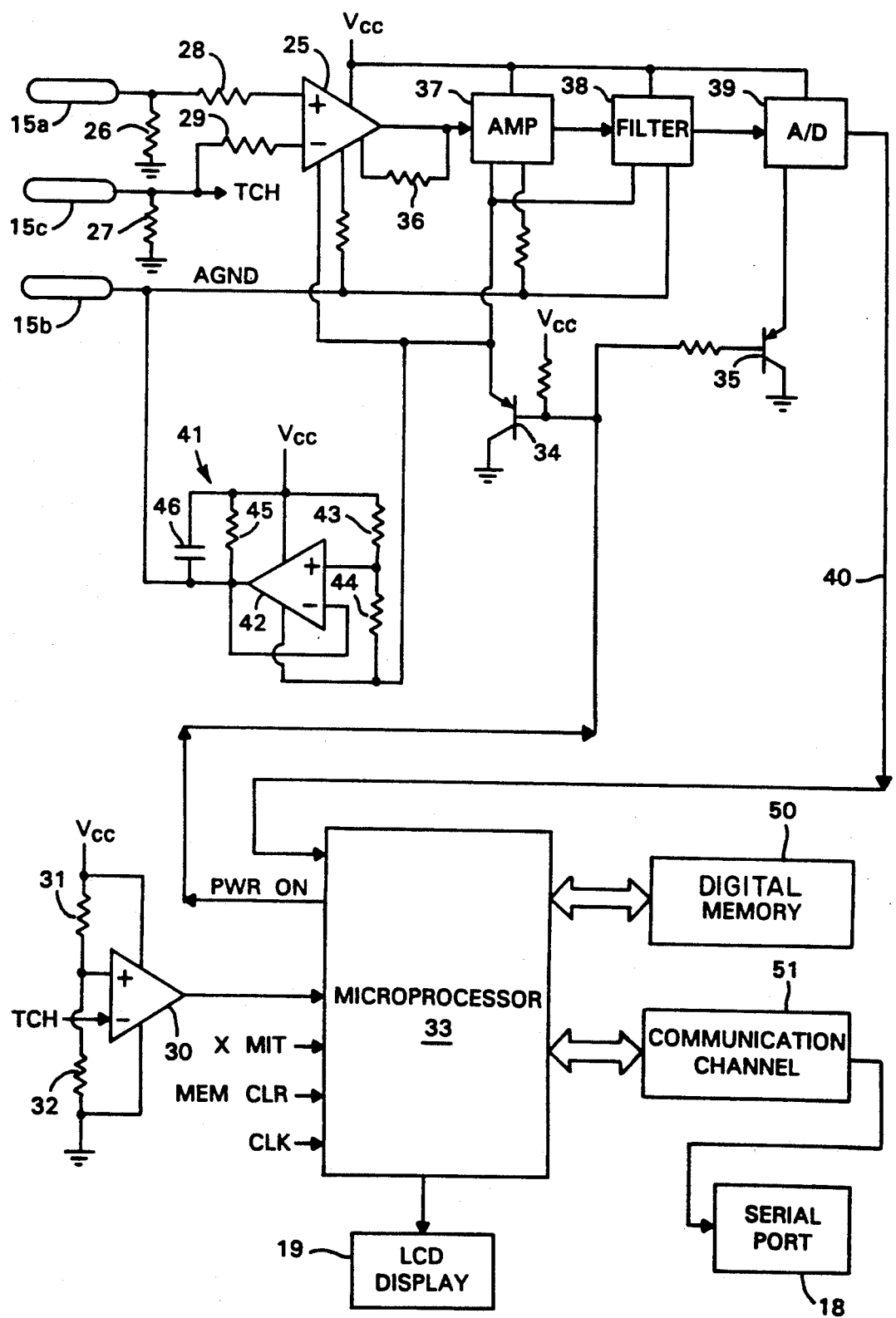
FIG. 2 is a circuit diagram of a portable ECG monitor/recorder exemplified by the present invention.

FIG. 2 illustrates the electronic components and circuitry contained in the casing 12 of the portable ECG monitor/recorder. As shown, two of the conductive electrodes 15a, 15c are coupled to the non-inverting and inverting inputs of an amplifier 25, and the third conductive electrode 15b provides an analog ground signal (AGND) to various electronic components. A first pair of resistors 26, 27 (preferably 22MΩ each) are respectively interposed between the two "hot" electrodes 15a, 15c and ground and provide the circuit with a high input impedance. The second pair of resistors 28, 29 (preferably 1MΩ each) are positioned between the electrodes and the inputs of the amplifier 25 and provide a simple patient protection/electrostatic discharge (ESD) network which protects the electronic circuitry from static discharge from the user and limits the maximum battery current applied to the user to approximately 2 microamps.

Upon contact of the conductive electrodes by the user, a touch signal (TCH) is generated and a differential ECG signal is applied to the inputs of the amplifier 25. The touch signal is applied to the inverting input of a comparator 30, which serves as a touch sensor. A divider network consisting of two resistors 31, 32 provides current from the power supply ($V_{cc}$)—preferably consisting of two 3 V lithium coin cell batteries wired in parallel—to the non-inverting input of the comparator 30. Since the inverting input is normally low, the output of the comparator is normally high (i.e., logic one). When the user contacts the electrodes, however, and the touch signal (TCH) is generated, the inverting input goes high and causes the output of the comparator 30 to go to logic zero. The signal from the comparator 30 is applied to an input of a microprocessor 33, which, when the touch sensor signal is low, provides a "power on" signal to the other circuit components. Thus, the electronic circuit components are only activated when the user grasps the conductive electrodes 15a–15c.

In the preferred embodiment the touch sensor consists of the depicted comparator 30 and divider network 31, 32, but it will be readily appreciated that other devices, such as a depletion-type MOSFET, can be effectively used as the touch sensor. For example, if a depletion-type MOSFET is used, the touch signal (TCH) is applied to the gate terminal, the source terminal is coupled to ground and the drain terminal is coupled to the microprocessor 33, whereby a logic zero signal is provided to the microprocessor when the user contacts the electrodes 15a–15c.

The "power on" signal (having a logic zero value) provided by the microprocessor 33 is applied to the base terminals of a pair of pnp type transistors 34, 35. These transistors are normally biased to an OFF condition due to the connection of the power supply $V_{cc}$ to their base terminals, but application of the logic zero "power on" signal to their bases turns them ON. This enables various electronic components in the signal processing circuitry.

As indicated previously, when a user contacts the electrodes, an analog ECG signal is applied to the inputs of the amplifier 25 (which, for example, may be implemented using a standard TLC251C operational amplifier). In accordance with an important aspect of the present invention, the output of this amplifier is not fed back to one of its inputs, but rather, is coupled through a resistor 36 to one of its compensating terminals (offset null pin 5—not shown) As a result of this arrangement, the gain of the amplifier is not controlled by feedback and a high common mode rejection ratio is achieved. The resistor 36 serves as a gain control. This amplifier arrangement also permits overall simplification of the circuitry, since only one additional amplifier is needed to get satisfactory performance. As will be appreciated, this significantly reduces the power consumption and spatial requirements of the circuit.

The output of amplifier 25 is applied to a second amplifier 37, which is configured in a typical feedback arrangement to provide a desired gain (for example, 4). The output of amplifier 37 is delivered to a standard monitor quality bandpass filter 38, consisting of a 40 Hz lowpass filter which eliminates some muscle artifact and 60 Hz interference, followed by a 0.5 Hz multiple feedback lowpass filter which minimizes baseline wander. Finally, the signal is digitized by an 8-bit analog-to-digital converter (A/D) 39 and is applied via data line 40 to the microprocessor 33.

A driver circuit 41, consisting of an amplifier 42, three resistors 43–45, and a capacitor 46, provide the amplifiers 25, 37 and filter circuit 38 with an analog ground (AGND) signal. This signal is normally held at $V_{cc}$(3 V) by the RC circuit consisting of resistor 45 and capacitor 46. When the user contacts the conductive electrode 15b, however, AGND is set to a value of $V_{cc}/2$ by the amplifier 42 and the divider network provided by resistors 43, 44.

During times when the user is contacting the electrodes 15a–15c and a logic zero interrupt signal is provided to the microprocessor 33 by the touch sensor 30, the microprocessor receives ECG data from the 8-bit A/D converter 39 and stores it in sequential memory address locations in a digital memory device 50. This memory device preferably consists of a 32K×8 static random access memory (SRAM), but it will be readily appreciated that the memory device could satisfactorily consist of a flash-EPROM or any read/write memory circuit configured as a first in/first out (FIFO) ring memory. The microprocessor 33 (which, for example, may consist of a Signetics 83CL410HFT processor) samples digitized data from the A/D converter 30 every 8 milliseconds and, therefore, assuming the memory device 50 is a 32K×8 SRAM, about four minutes of data can be stored.

The microprocessor operates in a playback (or transmit) mode when it receives a logic zero "transmit" signal (XMIT), which is generated when the user depresses the control button 16. In this playback mode, the microprocessor sequentially fetches the digitized ECG data from the digital memory device 50 and sends it to the serial port 18 in burst mode via a communication channel 51.

If the user depresses the second control button 17, a logic zero "memory clear" signal (MEM CLR) is provided to the microprocessor. If this signal is received simultaneously with depression of the "transmit" control button 16 by the user, the microprocessor instantaneously clears the digital memory 50 by resetting an internal write pointer to the starting base address of the memory. As will be appreciated, making the "memory clear" button 17 a slave to the "transmit" button 16 protects against accidental or inadvertent erasure of data.

Finally, the microprocessor also generates the information and provides the drive signals for the LCD display 19. These functions are executed under instructions from standard built-in firmware (not shown) in the microprocessor's internal memory.

Figure 3:
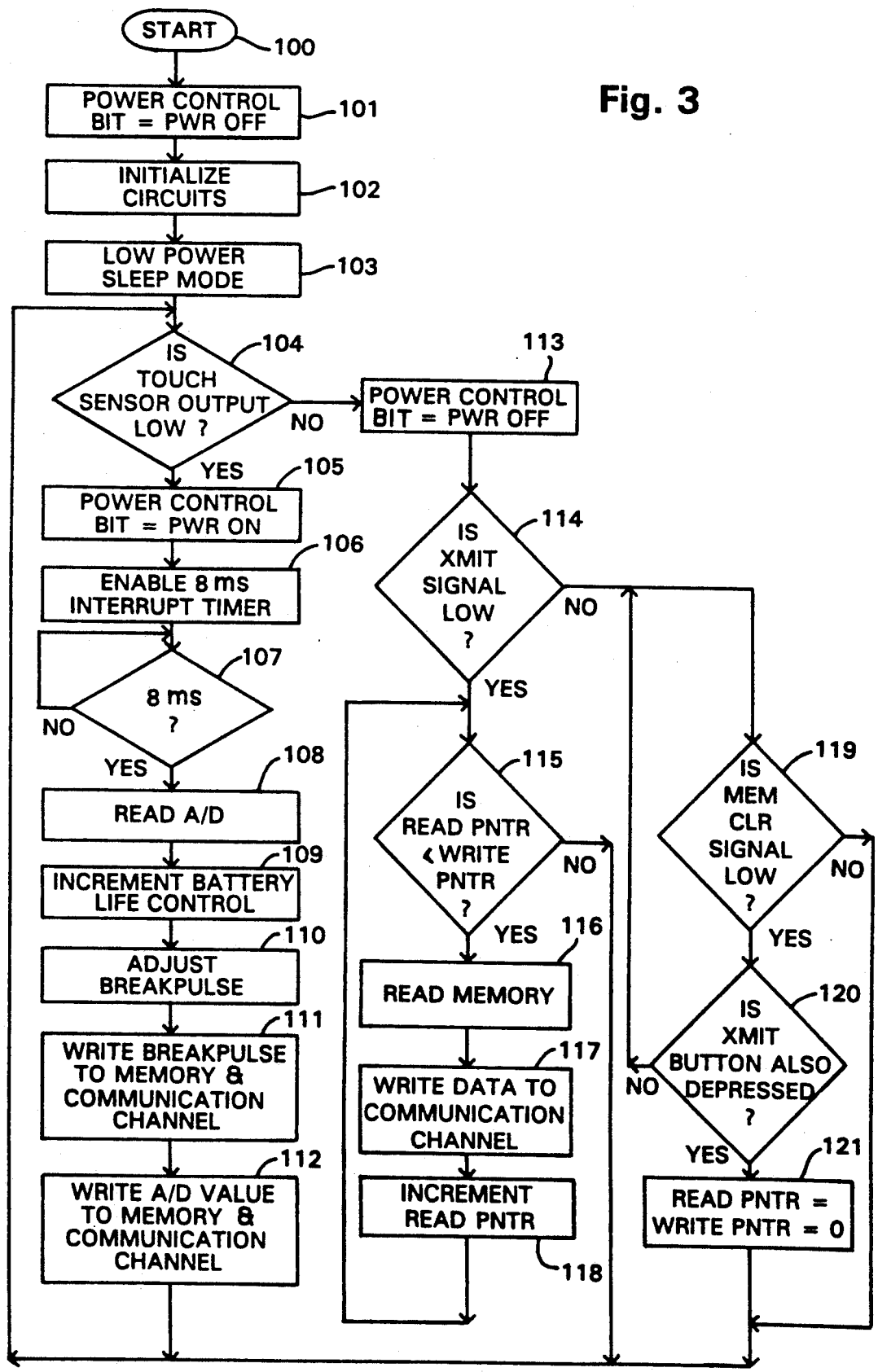
FIG. 3 is a flow chart representation of a preferred sequence of operations followed by the microprocessor of the inventive ECG monitor/recorder of FIG. 2.

The sequence of operations followed by the microprocessor 33 in the inventive ECG monitor/recorder is illustrated in further detail by the flow chart of FIG. 3. Specifically, this flow chart illustrates the record, transmit and memory clear modes of operation. When batteries are put in the device (step 100), the microprocessor sets its power control bit to a "power off", i.e., logic one, condition (step 101) and initializes the circuit components (step 102). This initialization includes setting both the read pointer and write pointer of the memory device 50 to a starting base (0) address, initializing the communication channel 51 to a master transmitter mode and initializing the port pins to minimize power consumption. After this is done, the microprocessor goes into a low power sleep mode (step 103), in which it waits for an interrupt signal and holds the circuit components in a non-enabled condition.

In sampling for interrupt signals, at step 104 the microprocessor determines the logic condition of the output signal of the touch sensor 30. If it is low, indicating that the user is contacting the electrodes 15a–15c, the microprocessor enables the circuit components by setting the power control bit to a "power on" (logic zero) condition (step 105). The user's analog ECG signal is then digitized, as discussed previously, and provided to the microprocessor on data line 40. Meanwhile, the microprocessor initiates an 8 millisecond sampling cycle (steps 106 and 107), whereby it reads the digitized output of the A/D converter 39 after 8 milliseconds have elapsed (step 108).

Next, the microprocessor increments a battery life control (step 109), which control is indicative of the remaining active life of the batteries. This control is used to adjust either the height or width of a break pulse (step 110) and the adjusted break pulse is written to both the memory device 50 and the communication channel 51 in real time (step 111). The break pulse is stored to indicate the beginning of a data sequence (or recording session), and also as an indicator of remaining battery life. When the batteries are new, the square wave break pulse has, for example, a three millivolt amplitude and an 80–100 millisecond duration. If the break pulse magnitude falls below one millivolt, or if the break pulse duration falls below about 25 milliseconds, a trained physician analyzing the data sequence will recognize that the remaining battery life is short and can alert the user to change the batteries. As a calibration feature, it may be desirable to have the microprocessor generate and store a 1 millivolt square wave pulse in conjunction with generating and storing the break pulse.

Once the break pulse has been stored in memory, the microprocessor sequentially writes the digitized ECG data to both the memory device 50 and the communication channel 51 in real time mode (step 112).

As long as the user contacts the conductive electrodes 15a–15c, the touch sensor output remains low and the microprocessor continues this 8 millisecond data sampling and storing cycle, except that a break pulse is generated only at the beginning of the new data sequence.

If, at step 104, it is determined that the user is not contacting any conductive electrodes, the microprocessor sets the power control bit to a "power off" (logic one) condition (step 113) and checks the logic condition of the "transmit" signal (step 114). When the "transmit" signal (XMIT) is low, indicating that the user has depressed control button 16 and desires to transmit the stored ECG data to an external receiver, the microprocessor enables only the circuitry of the communication channel 51. Next, at step 115, it is determined whether the address of the write pointer in the memory is greater than the address of the read pointer, and if it is, the contents of the memory at the read pointer address are read (step 116) and written to the communication channel 51 in burst mode (step 117). By transmitting in burst mode, four minutes of data can be sent out of the serial port in less than ten seconds. It will be appreciated, therefore, that power consumption during transmission of data is kept to a minimum, which effectively doubles the battery life. This is significant inasmuch as the batteries are difficult to change and typically cannot be changed by the user.

Once data at the read pointer address has been written to the communication channel, the read pointer is incremented (step 118) and the read/write cycle is continued until all of the data has been transmitted. As noted before, this entire data transmission procedure required less than ten seconds when the memory is full.

If it is determined at step 114 that the user does not desire data transmission, the microprocessor determines whether the "memory clear" signal (MEM CLR) is low (i.e., whether the user desires to clear the memory) (step 119). If not, the control sequence cycles back to step 104 and repeats. However, if a logic zero "memory clear" signal is received, and it is determined that the transmit control button 16 is being simultaneously depressed (step 120), both the internal read pointer and write pointer are set to the starting base address (0), thus, effectively clearing the memory (step 121).

Figure 4:
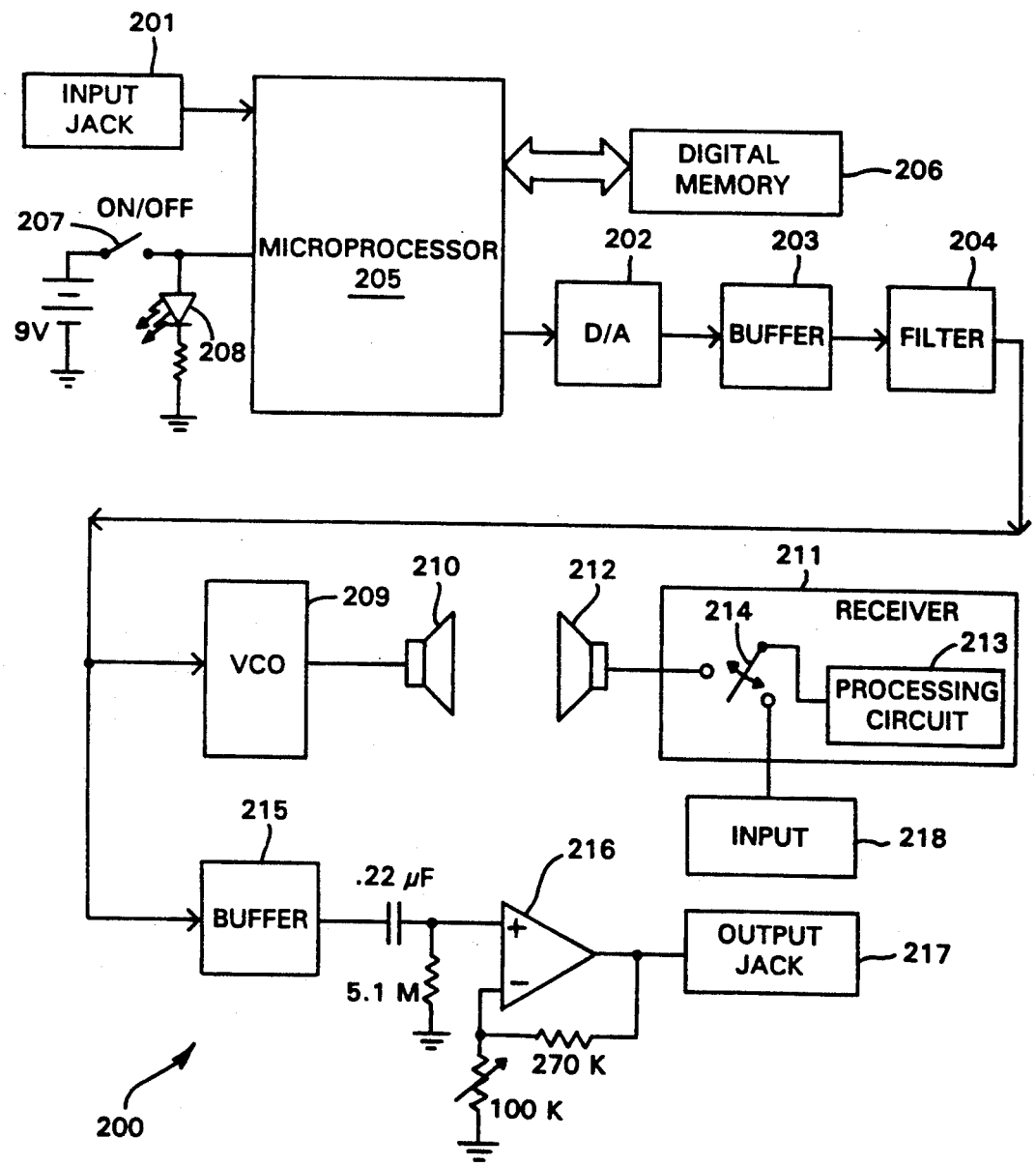
FIG. 4 is a circuit diagram of a data-converting modem for use in conjunction with the ECG monitor/recorder of FIG. 2.

In accordance with another important aspect of the present invention, a separate modem device is provided which is adapted for electrical connection to the ECG monitor/recorder 10 and includes components for receiving the digitized ECG data stored in the recorder's memory 50, processing that data into a format which can be transmitted for analysis to an external receiver, and transmitting the processed data to the external receiver. The circuit diagram of FIG. 4 illustrates the components of this modem, which is designated generally by reference numeral 200. An input jack 201 is adapted to mate with the output serial port 18 of the recorder 10 so that data transfer can be effected. The digitized ECG data from the recorder memory 50 is converted into analog signals having discrete voltage levels by a standard digital-to-analog converter (D/A) 202. Every 8 milliseconds, this D/A converter converts a data byte to a discrete voltage level. This voltage level is applied to a buffer 203 and an anti-aliasing 40 Hz lowpass filter 204 that smooths the voltage waveform back to its original analog shape.

In a preferred embodiment, the modem 200 includes a microprocessor 205 (for example, a Signetics 83CL410 processor) and a digital memory 206 (which is preferably an SRAM or an EPROM). A power source consisting of a common nine volt alkaline battery is coupled to the microprocessor through a switch 207, by means of which the user can turn the microprocessor (and, thus, the modem itself) on and off. An LED 208 provides a visual indicator to the user that the microprocessor 205 is being powered.

The microprocessor receives serial data from the recorder 10 via the serial input jack 201. This serial data is converted to 8-bit parallel (byte-wide) information by internal serial channel hardware, which data byte is then an exact copy of the sampled ECG data acquired by the recorder 10. The microprocessor 205 then stores the ECG data byte in the SRAM memory 206, and loops back to receive the next byte from the internal serial channel hardware.

Every 8 milliseconds, an internal timer generates an interrupt signal that directs the microprocessor 205 to fetch the next sequential byte of ECG data from the SRAM memory 206 and send it to the D/A converter 202. Because the D/A converter 202 can only reconstruct the sampled ECG waveforms at a rate of 1 byte every 8 milliseconds, burst mode transmission of data from the recorder 10 to the modem 200 would be impossible without the microprocessor 205 and the SRAM memory 206. The SRAM memory is used as an ECG data buffer, so that the recorder-to-modem data transmission can occur at a higher speed than the real-time playback of the modem, without inter-device synchronization problems.

The analog output of the filter 204 is fed to a voltage controlled oscillator (VCO) 209 that has a center frequency of 1900 Hz. The VCO 209 is calibrated such that its frequency deviates 100 Hz from its center frequency for every one millivolt change in the analog ECG waveform.

The output of the VCO 209 is coupled to a speaker 210, by means of which frequency modulated tones are audibly transmitted. An external receiver 211, such as an ECG monitor in a physician's office, may receive the frequency modulated tones from the speaker 210 via an appropriate audio receiver 212 (e.g., a telephone receiver). The received audio signals are then provided to processing circuitry 213 in the receiver 211 via a switching mechanism 214.

In a preferred embodiment, the modem 200 further includes a unity gain buffer 215 and an amplifier circuit (generally designated by reference numeral 216) which produces an output signal having an amplitude of 1 volt per millivolt amplitude in the analog ECG waveform received from the filter 204. This output signal is provided to an output jack 217 which may be coupled to a corresponding input jack 218 on the receiver 211 for effecting data transfer.

Figure 5:
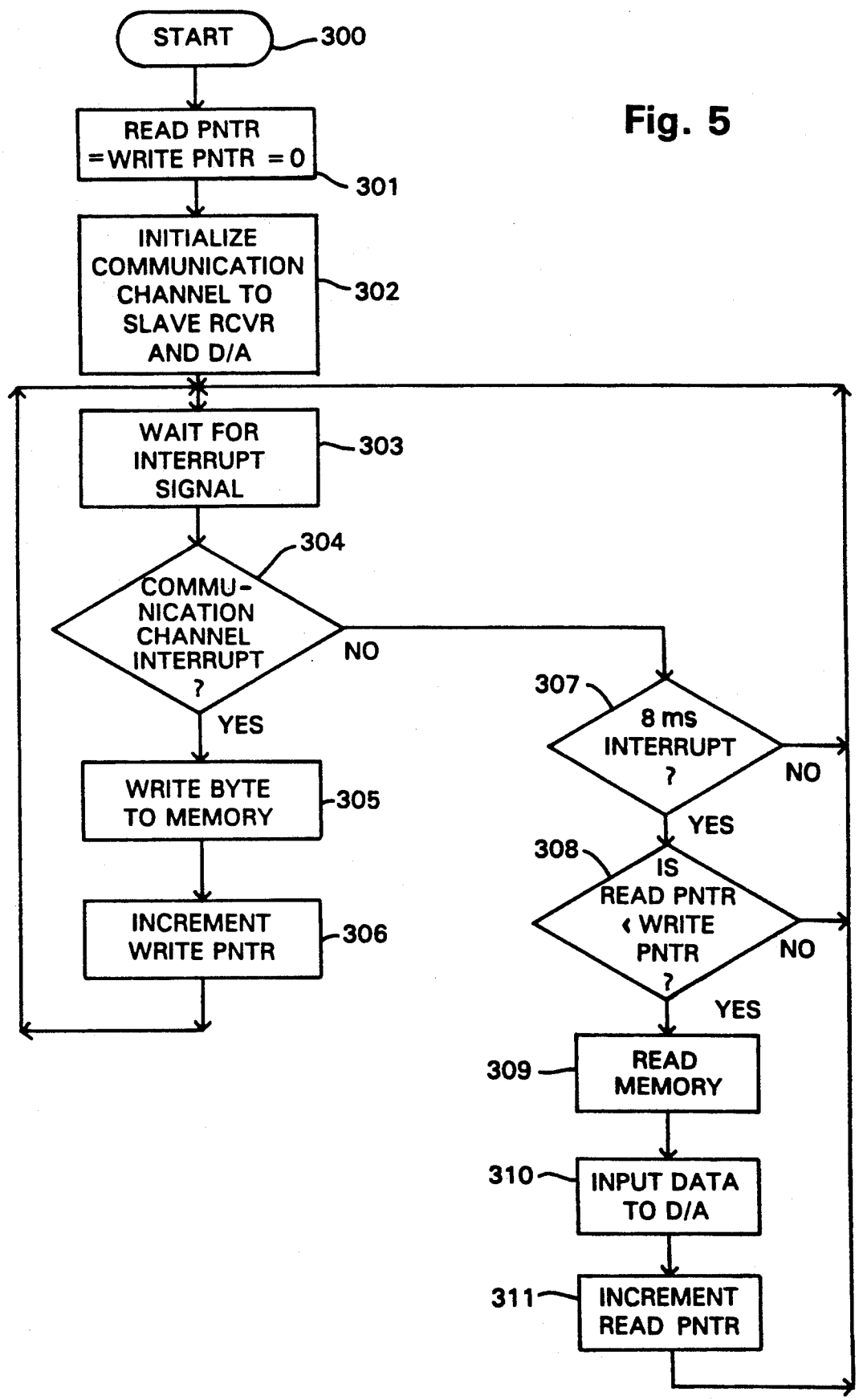
FIG. 5 is a flow chart representation of a preferred sequence of operations followed by the modem of FIG. 4.

The sequence of operations followed by the microprocessor 205 in the modem 200 is illustrated in further detail by the flowchart of FIG. 5. When the switch 207 is closed and the microprocessor is turned on (step 300), the microprocessor sets both the read pointer and write pointer of the memory device 206 to a starting base (0) address (step 301), initializes the communication channel to a slave receiver mode and initializes the D/A converter 202 (step 302). The modem then awaits for an interrupt signal (step 303). If an interrupt signal is received from the communication channel (step 304), an ECG data byte is written to the memory 206 (step 305) and the internal write pointer in the memory is incremented (step 306). This loop continues until the entire data sequence from the recorder is received and written to the memory 206 in the modem.

With respect to transmission of the data stored in the memory 206, when an 8 millisecond interrupt signal is received at step 307 and it is determined that the address of the internal write pointer is greater than the address of the internal read pointer (step 308), the sequential byte of ECG data stored at the read pointer address of the memory 206 is read (step 309). This byte of data is then sent to the D/A converter 202 for processing (step 310) and the internal read pointer is incremented (step 311). This loop is continued, with 8 millisecond sampling, until all of the data stored in memory 206 has been processed (i.e., until the read pointer address is the same as the write pointer address).

As can be seen from the foregoing detailed description, the present invention provides an improved apparatus for recording medical-grade ECG data and yet which is convenient and comfortable for a user to wear. This apparatus does not utilize paste-on electrodes. The inventive recorder has a high common mode rejection ratio due to the use of a three electrode configuration and a unique amplifier arrangement, and the design of the processing circuits insures long battery life. A separate, attachable modem device is provided for transmitting stored data from the recorder to a receiving station, this modem enabling transfer of data from the recorder in power-saving burst mode.

What is claimed is:

1. A system for selectively monitoring and recording a user's ECG data and transmitting such data to an external receiving station, comprising:

a portable recording unit having a casing which encloses electronic elements, including processing means, a power source and a first memory, and which carries three conductive electrodes that are electrically coupled to the electronic elements, a first one of the electrodes being disposed on a first surface of the casing for contact with an ECG lead position on the user's body and the other two electrodes being disposed on at least one other surface of the casing and positioned for ease of contact by the user with a thumb and finger, respectively, of a hand, whereby the unit monitors and processes the user's ECG data and stores it in memory only when the first electrode contacts a body lead position and the second and third electrodes are grasped by the user; and a modem which is adapted for electrical connection to the recording unit, comprising circuit means for processing the ECG data into a format which can be transmitted for analysis to the external receiving station and means for transmitting the processed ECG data to the external receiving station.

2. The system of claim 1, wherein one of the two electrodes disposed for contact by the user with a thumb and finger provides a ground signal source for the electronic elements.

3. The system of claim 1, wherein the recording unit includes a wristband for securing the casing to a wrist of the user and the first electrode is disposed on the back surface of the casing such that it lies in continuous electrical contact with the user's wrist.

4. The system of claim 1, wherein the casing is adapted such that the recording unit may be worn by the user as a pendant, the first electrode being disposed to facilitate electrical contact with an ECG lead position on the user's chest.

5. The system of claim 1, wherein the casing of the recording unit is adapted to facilitate hand-held use by the user.

6. The system of claim 1, wherein the processing means of the recording unit comprises:

circuitry coupled to the power source and the electrodes for receiving the user's analog ECG data and converting such data into digitized format; and a microprocessor for controlling storage of the digitized ECG data into the first memory.

7. The system of claim 6, wherein the microprocessor in the recording unit is activated only when the user grasps the second and third electrodes.

8. The system of claim 6, wherein the recording unit further comprises an output terminal which is coupled to the first memory and adapted for connection to an input terminal of the modem, the microprocessor in the recording unit, upon command of the user, controlling the transmission of the digitized data from the first memory to the input of the modem.

9. The system of claim 8, wherein the modem further comprises a second memory for receiving and storing ECG data from the first memory of the recording unit and a microprocessor for controlling the passage of ECG data to and from the second memory and to the circuit means.

10. The system of claim 9, wherein the digitized data is transmitted to the modem in burst mode, thereby minimizing power consumption.

11. The system of claim 1, wherein the circuit means in the modem converts the ECG data into an audio signal format.

12. The system of claim 11, wherein the transmitting means comprises a speaker by which the audio signal ECG data may be provided telephonically to the external receiving station.

13. The system of claim 1, wherein the circuit means in the modem converts the ECG data into an analog signal format.

14. The system of claim 13, wherein the transmitting means comprises an output jack by which the analog signal ECG data may be coupled to an input terminal of the external receiving station.

15. A system for selectively monitoring and recording a user's electrocardiographic (ECG) data and transmitting such data to an external receiving station, comprising:

a wrist-worn recording unit having a casing with front, back and side surfaces which encloses electronic elements, including processing means, a power source and a first memory, and which carries a pair of conductive electrodes that are electrically coupled to the electronic elements, one of the electrodes being disposed on the back surface of the casing such that it lies in continuous electrical contact with the user's wrist and the second electrode being disposed on a surface of the casing other than the back surface and positioned for ease of contact by the user with the hand opposite the contacted wrist, whereby the unit monitors and processes the user's ECG data and stores it in memory only when the user touches the second electrode; and a modem adapted to receive ECG data from the first memory of the recording unit, comprising circuit means for processing the ECG data into a format which can be transmitted for analysis to the external receiving station and means for transmitting the processed ECG data to the external receiving station.

16. The system of claim 15, wherein the recording unit further includes a third conductive electrode electrically coupled to the electronic elements, the third electrode being disposed on a surface of the casing other than the back surface and positioned for ease of contact by the user with the hand opposite the contacted wrist, whereby a ground signal is provided to the electronic elements when the user contacts the third electrode.

17. The system of claim 15, wherein the recording unit and the modem are provided as separate devices, the recording unit and the modem being adapted such that ECG data can be transmitted from the first memory to the modem.

18. The system of claim 15, wherein the processing means of the recording unit comprises:

circuitry coupled to the power source and the electrodes for receiving the user's analog ECG data and converting such data into digitized format; and a microprocessor for controlling storage of the digitized ECG data into the first memory.

19. The system of claim 18, wherein the microprocessor in the recording unit is activated only when the user touches the second electrode.

20. The system of claim 18, wherein the recording unit further comprises an output terminal which is coupled to the first memory and adapted for connection to an input terminal of the modem, the microprocessor in the recording unit, upon command of the user, controlling the transmission of the digitized data from the first memory to the input of the modem.

21. The system of claim 20, wherein the modem further comprises a second memory for receiving and storing ECG data from the first memory of the recording unit and microprocessor for controlling the passage of ECG data to and from the second memory and to the circuit means.

22. The system of claim 21, wherein the digitized data is transmitted to the modem in burst mode, thereby minimizing power consumption.

23. The system of claim 15, wherein the circuit means in the modem converts the ECG data into an audio signal format.

24. The system of claim 23, wherein the transmitting means comprises a speaker by which the audio signal ECG data may be provided telephonically to the external receiving station.

25. The system of claim 15, wherein the circuit means in the modem converts the ECG data into an analog signal format.

26. The system of claim 25, wherein the transmitting means comprises an output jack by which the analog signal ECG data may be coupled to an input terminal of the external receiving station.

27. A system for selectively monitoring and recording a user's electrocardiographic (ECG) data and transmitting such data to an external receiving station, comprising:

a wrist-worn recording unit having a casing which encloses electronic elements, including a processing means, a power source and a first memory, and which carries first and second conductive electrodes that are electronically coupled to the electronic elements, the electrodes being disposed on different exterior surfaces of the recording unit, whereby the unit monitors and processes the user's ECG data and stores it in memory only when the user touches both of the electrodes; and a modem adapted to receive ECG data from the first memory of the recording unit, comprising circuit means for processing the ECG data into a format which can be transmitted for analysis to the external receiving station and means for transmitting the processed ECG data to the external receiving station.

28. The system of claim 27, wherein the first electrode is disposed on a back surface of the recording unit such that it lies in continuous electrical contact with the user's wrist, and the second electrode is disposed on a surface of the recording unit other than the back surface and is positioned for ease of contact by the user with the hand opposite the contacted wrist.

29. The system of claim 27, wherein the recording unit and the modem are provided as separate devices, the recording unit and the modem being adapted such that ECG data can be transmitted from the first memory to the modem.

30. The system of claim 27, wherein the circuit means in the modem converts the ECG data into an audio signal format.

31. The system of claim 30, wherein the transmitting means comprises a speaker by which the audio signal ECG data may be provided telephonically to the external receiving station.

32. The system of claim 27, wherein the circuit means in the modem converts the ECG data into an analog signal format.

33. The system of claim 32, wherein the transmitting means comprises an output jack by which the analog signal ECG data may be coupled to an input terminal of the external receiving station.

* * * * *